United States Patent [19]

Li

[11] 4,183,828
[45] Jan. 15, 1980

[54] CATALYST FOR DEHYDROCOUPLING PROCESS

[75] Inventor: Tao P. Li, Chesterfield, Mo.

[73] Assignee: Monsanto Company, St. Louis, Mo.

[21] Appl. No.: 884,795

[22] Filed: Mar. 9, 1978

Related U.S. Application Data

[62] Division of Ser. No. 735,865, Oct. 27, 1976, Pat. No. 4,091,044.

[51] Int. Cl.² .......................... B01J 23/14; B01J 23/18
[52] U.S. Cl. .................................................. 252/461
[58] Field of Search .......................... 252/461; 423/593

[56] References Cited

U.S. PATENT DOCUMENTS

| | | | |
|---|---|---|---|
| 3,476,747 | 11/1969 | Hargis et al. | 260/669 R |
| 3,557,235 | 1/1971 | Henry et al. | 260/670 X |
| 3,984,353 | 10/1976 | Sergunkin et al. | 252/461 |
| 4,066,704 | 1/1978 | Harris et al. | 252/461 X |

Primary Examiner—W. J. Shine
Attorney, Agent, or Firm—James C. Bolding

[57] ABSTRACT

Toluene and toluene derivatives are oxidatively dehydrocoupled to produce stilbene and stilbene derivatives by heating toluene or a toluene derivative in the vapor phase with a metal- and oxygen-containing composition which functions as an oxidant or oxygen carrier and has the empirical formula $$Sb_aPb_bBi_cO_d$$

wherein a is 1, b is 0.2–10, c is 0–5 and d is a number taken to satisfy the average valences of the Sb, Pb and Bi in the oxidation states in which they exist in said composition. Alternatively, the same metal- and oxygen-containing composition can be employed as a catalyst for the dehydrocoupling reaction when oxygen or an oxygen-containing gas is heated with the hydrocarbon reactant.

2 Claims, No Drawings

CATALYST FOR DEHYDROCOUPLING PROCESS

This is a division of application Ser. No. 735,865, filed Oct. 27, 1976, now U.S. Pat. No. 4,091,044.

BACKGROUND OF THE INVENTION

The present invention relates to the production of 1,2-diphenylethylene (stilbene) and derivatives thereof.

Stilbene, because of its unsaturated character, is very reactive and may be employed in various organic syntheses. It is useful in the production of products which may be used in the manufacture of dyes, paints and resins. It is also useful in optical brighteners, in pharmaceuticals and as an organic intermediate.

Heretofore, stilbene has not been available in commercial quantities because the attendant yields of the known processes for the manufacture of stilbene have been generally small. Stilbene has been synthesized by dehydrogenation of bibenzyl; by dehydrogenation of 1,2-bis(3-cyclohexen-1-yl)ethylene (U.S. Pat. No. 3,387,050); and by reacting a benzyl mercaptan with a sulfactive catalyst, for example, molybdenum disulfide and copper sulfide (U.S. Pat. No. 2,645,671). Stilbene and halostilbenes have been synthesized by the iodative dehydrocoupling of toluene and halogen-substituted toluenes with elemental iodine and molten lithium iodide at toluene conversions of 10–30% (U.S. Pat. No. 3,409,680).

In U.S. Pat. No. 3,205,280, a catalytic dehydrogenation process is disclosed wherein certain hydrocarbons are converted to less saturated hydrocarbons by heating a mixture of hydrocarbon with at least 0.001 mol of a halogen per mol of hydrocarbon in the presence of free oxygen and a solid catalyst of an alkali metal halide and silver halide and additionally oxides and halides of certain elements.

In U.S. Pat. No. 3,694,518, a dehydrocoupling process is disclosed wherein toluene is converted to stilbene by heating toluene with oxygen in the presence of iodine and, optionally, an inert heat carrier material. In U.S. Pat. No. 3,868,427 this process of dehydrocoupling is carried out in the presence of a metal oxide, preferably palladium oxide coated on alpha-alumina.

Dehydrocoupling of toluene by the reaction with lead oxide to form stilbene has been reported by Behr and Van Dorp, Chem. Ber. 6,753 (1873) and Lorenz, Chem. Ber. 7,1096 (1874). In this reported work, stilbene is obtained by conveying toluene over lead oxide maintained at or about at a dark red glow. More recent disclosures of the metal oxide-toluene reaction are given in U.S. Pat. No. 3,476,747 and U.S. Pat. No. 3,494,956. The former patent relates to preparation of 1,2-bis(aryl)ethylenes by contacting of an aryl methane such as toluene with an inorganic oxidant from the group of arsenic pentoxide, antimony pentoxide, bismuth trioxide, manganese arsenate, or antimony tetraoxide at elevated temperatures. In Example 9 of U.S. Pat. No. 3,494,956, it is reported that a mixture of toluene and oxygen passed over heated lead oxide produces bibenzyl. In another patent, U.S. Pat. No. 3,557,235, it is reported that toluene can be oxidatively coupled in a stoichiometric reaction where a metal oxide, such as lead oxide, serves as a source of oxygen in the reaction.

SUMMARY OF THE INVENTION

This invention is directed to an improved dehydrocoupling process for converting toluene and toluene derivatives to stilbene and stilbene derivatives. Accordingly, typical objects of the invention are to provide an improved one-step, vapor-phase process for the production of stilbene and derivatives thereof and to provide a vapor-phase dehydrocoupling process for converting toluene and toluene derivatives to stilbene and stilbene derivatives characterized by high toluene conversion and high stilbene selectivity.

Other objects, aspects and advantages of the invention will become apparent to those skilled in the art upon further study of the disclosure and the appended claims.

In accordance with the invention, toluene and toluene derivatives are oxidatively dehydrocoupled to produce stilbene and stilbene derivatives by heating the toluene or toluene derivatives in the vapor phase in contact with a metal- and oxygen-containing composition which functions as an oxidant or oxygen carrier or as a catalyst, said composition having the following empirical formula

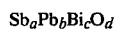

$$Sb_aPb_bBi_cO_d$$

wherein a is 1, b is 0.2–10, c is 0–5 and d is a number taken to satisfy the average valences of the Sb, Pb and Bi in the oxidation states in which they exist in the oxidant or catalyst. Preferred compositions are those defined by the formula

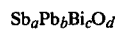

$$Sb_aPb_bBi_cO_d$$

wherein a is 1, b is 0.5–5, c is 0–1 and d is a number taken to satisfy the average valences of the Sb, Pb and Bi in the oxidation states in which they exist in the oxidant or catalyst. The metals are in combination with oxygen and may exist as individual oxides or as complexes of two or more of the metals and oxygen or as a combination of oxides and complexes. The reduced form of the oxidant remaining after the reaction can be regenerated by air oxidation in the absence of the hydrocarbon and reused.

The same metal- and oxygen-containing composition described above can be employed as a catalyst for the conversion of toluene and toluene derivatives to stilbene and stilbene derivatives. When operating in the catalytic mode, the hydrocarbon together with oxygen is heated in the vapor phase in contact with the metal- and oxygen-containing composition described above.

DESCRIPTION OF THE PREFERRED EMBODIMENTS

The process of the invention is conveniently carried out in an apparatus of the type suitable for carrying out chemical reactions in the vapor phase. It can be conducted in a single reactor or in multiple reactors using either a fixed bed, a moving bed or a fluidized bed system to effect contacting of the reactant or reactants and oxidant or catalyst. The reactant toluene or toluene derivative will generally be heated and introduced into the reactor as a vapor. However, the reactant may be introduced to the reactor as a liquid and then vaporized.

The temperature range under which the reaction can be carried out extends from about 500° C. to about 650° C. preferably from about 540° to about 600° C. Pressure is not critical and the reaction may be carried out at subatmospheric, atmospheric or superatmospheric pressure as desired.

The contact time of the reactant hydrocarbon and the oxidant or catalyst in the reactor may vary depending upon the reaction temperature and the desired toluene conversion level. At higher temperatures and lower toluene conversion levels, shorter contact times are required. Generally, the contact time will vary from about 0.5 second to about 5 seconds. Preferably, for optimum conversion and selectivity in the preferred temperature range, a contact time from about 2 sec. to about 4 sec. is employed.

In addition to the toluene and/or toluene derivatives, other inert substances such as nitrogen, helium, and the like may be present in the reactor. Such inert materials may be introduced to the process alone or may be combined with the other materials as feed. Water or steam may be added to the reaction zone preferably being introduced with the feed in order to improve the selectivity to the desired products and particularly to suppress complete oxidation to $CO_2$. Steam-to-hydrocarbon ratios in the range from 0.5 to 10 or more are suitable, the upper limit being determined by practical cost considerations. Ratios in the range from 1 to 3 are preferred.

The reaction may be conducted in the presence or absence of added free oxygen. When oxygen is not fed with the hydrocarbon, the oxygen required for the reaction is provided by the metal- and oxygen-containing composition which enters into the reaction and is consequently reduced during the course of the reaction. This necessitates regeneration or re-oxidation which can be easily effected by heating the material in air or oxygen at temperatures from about 500° to about 650° C. for a period of time ranging from about 30 min. to about one hour. In a semi-continuous operation, regeneration can be effected by periodic interruption of the reaction for re-oxidation of the metal- and oxygen-containing composition, i.e., periods of reaction are cycled with periods of regeneration. Operation, however, can be on a continuous basis whereby a portion of the metal- and oxygen-containing composition can be continuously or intermittently removed, re-oxidized and the re-oxidized material can thereafter be continuously or intermittently returned to the reaction. The latter method is particularly adapted to operations in which the metal- and oxygen-containing composition is fed in the form of a fluidized bed or a moving bed system.

When oxygen is employed as a reactant, sufficient oxygen is used to provide a hydrocarbon-to-oxygen mol ratio from about 1 to about 8 and preferably from about 2 to about 6. The oxygen may be supplied either as free oxygen or as an oxygen-containing gas such as air.

Suitable oxidants or catalysts can be prepared in several ways. The simplest method involves adding the metal oxides to water with stirring, heating the mixture to evaporate the water, drying and calcining. In another method of preparation, the powdered metal oxides can be intimately mixed before forming a paste of them with water and further mixing said paste. The paste can be spread and dried in air, after which it can be calcined in air. The calcined product can then be crushed and sieved to the desired mesh size. Alternatively, the metal oxides can be mixed dry together with a material which facilitates forming the mixture into pellets and then pressed to form pellets which are calcined prior to use.

The oxidant or catalyst may be employed alone or with a support. Suitable supports, for example, include silica, alumina, silica-alumina, metal aluminates such as magnesium aluminate and the like.

Temperatures employed for calcination of the metal- and oxygen-containing compositions may vary from about 400° to about 1200° C. The higher temperatures from about 900° to 1100° C. result in higher selectivity with some loss in activity. Preferred calcination temperatures, therefore, lie in the range from about 700° to about 1000° C. Calcination times may vary from about one to about six hours and preferably from about two to about four hours at the higher temperatures. The surface area of the oxidant or catalyst is not critical and may vary from about 0.1 $m^2/g$ to about 5.0 $m^2/g$.

The invention is illustrated in the following examples which, however, are not to be considered as limiting it in any manner whatsoever.

EXAMPLE 1

An oxidant was prepared by adding 58.3 g of antimony trioxide ($Sb_2O_3$) and 134 g of litharge (PbO) to 250 ml of water with stirring. This mixture was heated to evaporate the water and the resulting solid was dried in an oven at 110° C. overnight. A portion of the solid was calcined at 400° C. for 1 hr, then at 600° C. for 4 hr. and finally at 950° C. for 3 hr. The final product had an Sb/Pb atomic ratio of 1:1.5.

A stainless steel tube ½ in. in diameter and about 10 inches long was employed as a reactor for the toluene conversion reaction. It was equipped at the upper end with inlet means for introducing the reactant and at the bottom with outlet means for collection of the reaction effluent or for introducing it into a gas chromatograph for analysis. A charge of approximately 25 g of the oxidant described in the preceding paragraph was contained in the reactor being held in place with a coarse stainless steel frit at each end. In a series of runs, steam and toluene in a 1:1 mol ratio were fed to the reactor maintained at a pressure of 745 mm Hg and 560° C. at such a rate as to provide a 4-second residence time of toluene therein and a reaction period of about one minute. Between runs the oxidant was regenerated by passing air through it at a temperature of 560° C. for a period from about 30 to 60 minutes. Results of the runs in terms of toluene reacted (conversion) and the amount of the toluene reacted converted to stilbene (stilbene selectivity) are presented in Table 1 below.

Table 1

| Run No. | 1 | 2 | 3 | 4 |
| --- | --- | --- | --- | --- |
| Conversion, % | 53.1 | 41.0 | 37.0 | 36.9 |
| Selectivity, % | | | | |
| cis-stilbene | 6.8 | 6.8 | 6.8 | 6.8 |
| trans-stilbene | 58.9 | 58.3 | 58.5 | 57.9 |
| Bibenzyl | 5.0 | 7.3 | 7.7 | 8.4 |
| Benzene | 17.5 | 16.3 | 16.1 | 16.1 |
| $CO_2$ | 1.7 | 1.5 | 1.3 | 1.5 |

EXAMPLE 2

A series of oxidants having Sb/Pb atomic ratios of 1 to 5 were prepared for testing as oxidants in the dehydrocoupling of toluene to produce stilbene. Powdered lead oxide (PbO) and antimony oxide ($SbO_3$) were intimately mixed and a paste was formed of the mixture with distilled water which was also thoroughly mixed. The paste was spread to a depth of about 4 mm in a pan and dried in air on a hot plate at about 150° C. The very soft cake was transferred to an Alundum crucible and calcined in air for two hours at 600° C. After calcination, the very hard composition was crushed in a mortar and then sieved to 4 to 30 mesh size before evaluation.

A series of runs was conducted in which toluene was dehydrocoupled at a temperature of 560° C., a steam/toluene mol ratio of 2.0 and a contact time of 4.23 seconds using lead oxide (Run No. 1) and the various oxidants prepared as described above. The reactor employed was essentially the same as that in Example 1 except that it contained a concentric thermocouple. About 18 ml (~25 g) of the oxidant was contained in the reactor. Toluene and steam were metered into the inlet system through flash vaporizers using syringe pumps and passed through the oxidant in the reactor over a period of about 3 minutes. The reaction effluent was introduced into a gas chromatograph for analysis. Results are presented in Table 2 below. All tabulated results are averages of duplicate runs.

Table 2

| Run No. | 1 | 2 | 3 | 4 | 5 | 6 | 7 |
|---|---|---|---|---|---|---|---|
| Sb/Pb, Atomic | 0 | 1:1 | 1:1.25 | 1:1.5 | 1:2 | 1:2.5 | 1:5 |
| Surface area, m²/g | 0.13 | 0.37 | 0.60 | — | 0.25 | 0.21 | 0.39 |
| Conversion, % | 22.5 | 17.6 | 50.3 | 70.8 | 71.0 | 79.0 | 51.1 |
| Selectivity, % | | | | | | | |
| cis-stilbene | 7.1 | 2.3 | 3.8 | 3.8 | 3.7 | 2.5 | 5.6 |
| trans-stilbene | 61.1 | 19.3 | 32.6 | 32.3 | 28.5 | 21.7 | 48.3 |
| Bibenzyl | 7.6 | 23.9 | 8.2 | 2.2 | 3.0 | 1.7 | 5.8 |
| Benzene | 16.1 | 34.7 | 33 | 44.6 | 44.0 | 48.5 | 17.7 |
| CO₂ | 1 | 9.7 | 8.5 | 5.4 | 9.6 | 14.9 | 12.5 |

EXAMPLE 3

An oxidant having a Sb/Pb atomic ratio of 1:2 and a surface area of 0.37 m²/g was prepared as described in Example 2 above and recalcined at 900° C. for 3 hours. This oxidant was charged to the same reactor used in Example 2 and a series of runs were made in which steam and toluene (2:1) were contacted with the oxidant in the reactor over a 3-minute reaction period and the reaction effluent was analyzed by gas chromatographic means. Reaction conditions and results are presented in Table 3 below.

Table 3

| Run No. | 1 | 2 | 3 | 4 | 5* | 6 | 7 | 8 | 9 |
|---|---|---|---|---|---|---|---|---|---|
| Temperature, °C. | 570 | 590 | 560 | 570 | 580 | 580 | 580 | 590 | 600 |
| Contact Time, Sec. | 1.28 | 1.28 | 1.98 | 2.68 | 1.98 | 3.40 | 0.74 | 2.68 | 1.98 |
| Conversion, % | 15.7 | 15.43 | 26.9 | 29.5 | 26.6 | 42.8 | 12.5 | 39 | 28 |
| Selectivity, % | | | | | | | | | |
| cis-stilbene | 57.1 | 52.4 | 65.2 | 65.5 | 61.8 | 59.7 | 44.5 | 60 | 53.9 |
| trans-stilbene | | | | | | | | | |
| Bibenzyl | 27.4 | 29.4 | 16.3 | 13.8 | 17 | 8.7 | 38.7 | 11 | 18.2 |
| Benzene | 6.4 | 8.3 | 8.6 | 9.4 | 9.9 | 15.2 | 6.5 | 13.6 | 13.1 |
| CO₂ | 2.1 | 3.6 | 3.4 | 3.7 | 3.6 | 6.9 | 3.7 | 5.9 | 6.6 |

*Average of 3 runs (cis-stilbene and trans-stilbene selectivity values are combined.)

EXAMPLE 4

An oxidant was prepared as in Example 2, above, and recalcined at 800° C. for 2 hours and then at 900° C. for 3 more hours. The Sb/Pb atomic ratio of this composition was 1:2. It was employed in the same reactor used in Examples 2 and 3 and the dehydrocoupling of toluene was carried out in the reactor as previously described in these examples using various steam-toluene ratios. Reaction temperature was 560° C. and contact time was about 4.23 seconds. Other conditions and results are presented in Table 4 below.

Table 4

| Run No. | 1 | 2 | 3 | 4 | 5 | 6 | 7 | 8 | 9 | 10 | 11 | 12 |
|---|---|---|---|---|---|---|---|---|---|---|---|---|
| Steam/Toluene | 2.0 | 2.0 | 2.0 | 2.0 | 0.48 | 0.48 | 0.48 | 0.48 | 0 | 0 | 0 | 0 |
| Reaction Time, min. | 1 | 3 | 5 | 7 | 1 | 3 | 5 | 7 | 1 | 3 | 5 | 7 |
| Conversion, % | 65.3 | 40.8 | 30.5 | 20.9 | 53.3 | 29.2 | 17.3 | 11.8 | 41.7 | 16.5 | 9.4 | 7.9 |
| Selectivity, % | | | | | | | | | | | | |
| cis-stilbene | 6.3 | 7.0 | 6.8 | 5.9 | 5.2 | 5 | 3.00 | 2.00 | 5 | 1.2 | 0.9 | 0.6 |
| trans-stilbene | 54.3 | 60.4 | 58.7 | 50.7 | 44.4 | 42.7 | 25.8 | 17.2 | 42.9 | 15.9 | 7.4 | 4.9 |
| Bibenzyl | 3.8 | 8.3 | 11.6 | 17.7 | 6.9 | 20.1 | 30.4 | 30.8 | 15.1 | 31.9 | 23.4 | 17.7 |
| Benzene | 21.6 | 13.8 | 13.6 | 15.4 | 22.1 | 15.4 | 20.4 | 25.9 | 18.7 | 21 | 30.3 | 34.5 |
| CO₂ | 3.5 | 2.0 | 2.0 | 3.9 | 9.0 | 7.6 | 12.8 | 16.9 | 8.9 | 22.9 | 32.8 | 37.5 |

EXAMPLE 5

Another series of runs were made wherein toluene as dehydrocoupled in the same apparatus and following the same procedure given in Examples 2-4. In these runs, a masterbatch of oxidant having an Sb/Pb atomic ratio of 1:2 was prepared in the manner described in Example 2 and samples of this masterbatch were then recalcined at various temperatures for various periods of time. The samples were then evaluated as oxidants in the dehydrocoupling of toluene in the same apparatus and using the same method used in Examples 2-4. Reaction temperature was 560° C., a contact time of 4.2 seconds was used, the ratio of steam to toluene of the feed was 2.0 and the reaction time was 3 minutes. Results obtained at the various calcination temperatures and times are presented in Table 5 below.

Table 5

| Run No. | 1 | 2 | 3 | 4 | 5 | 6* | 7 | 8 | 9 | 10 |
|---|---|---|---|---|---|---|---|---|---|---|
| Calcining Temp. °C. | 600 | 700 | 800 | 800 | 900 | 900 | 900 | 1000 | 1000 | 1100 |
| Calcining Time, hr | 2.0 | 3.0 | 2.0 | 4.0 | 1.0 | 3.0 | 5.0 | 2.0 | 4.0 | 3.0 |
| Surface area, m²/g | 0.37 | 0.32 | 0.25 | 0.26 | 0.28 | 0.22 | 0.22 | 0.21 | 0.15 | 0.26 |
| Conversion, % | 80.2 | 79.4 | 62.9 | 63.2 | 57 | 51.2 | 45.7 | 24.1 | 16.3 | 15.7 |
| Selectivity, % | | | | | | | | | | |
| cis-stilbene | 40.2 | 37.9 | 52.6 | 53.5 | 58.6 | 65.9 | 68.5 | 49.2 | 35.8 | 31.8 |

Table 5-continued

| Run No. | 1 | 2 | 3 | 4 | 5 | 6* | 7 | 8 | 9 | 10 |
| --- | --- | --- | --- | --- | --- | --- | --- | --- | --- | --- |
| trans-stilbene | | | | | | | | | | |
| Bibenzyl | 1.9 | 1.8 | 3.5 | 3.3 | 4.7 | 4.1 | 6.7 | 29.5 | 36.4 | 43.5 |
| Benzene | 34.9 | 38.1 | 24.9 | 24.8 | 19.7 | 15.6 | 12.8 | 8.5 | 12.7 | 8.8 |
| $CO_2$ | 11.4 | 11.2 | 7 | 7 | 6.5 | 5.2 | 3.9 | 4.6 | 6.7 | 7.7 |

*Average of 3 runs

EXAMPLE 6

An oxidant was prepared by adding 58.3 g of $Sb_2O_3$, 134 g of PbO and 23.3 g of $Bi_2O_3$ in sequence to 250 ml of water with stirring. The resulting slurry was heated with stirring to evaporate the water. The remaining solid was dried in an oven at 110° C. overnight and then calcined at 900° C. for two hours. The finished oxidant had an Sb/Pb/Bi atomic ratio of 1:1.5:0.25 and a surface area of 0.42 m$^2$/g.

The oxidant prepared as described above was employed in a series of runs wherein toluene and steam in a mol ratio of 1:2 were contacted at various conditions with the oxidant contained in the reactor described in Example 2 and following the procedure described in that example. Reaction conditions and the results obtained are presented in Table 6 below.

Table 6

| Run No. | 1 | 2 | 3 | 4 | 5 | 6 | 7 |
| --- | --- | --- | --- | --- | --- | --- | --- |
| Temperature, °C. | 560 | 560 | 580 | 580 | 580 | 580 | 580 |
| Contact Time, sec. | 4.23 | 4.23 | 1.42 | 1.42 | 1.42 | 1.42 | 1.42 |
| Reaction Time, min. | 1 | 3 | 1 | 3 | 5 | 7 | 0.17 |
| Conversion, % | 74.5 | 53.2 | 47.3 | 23.2 | 14 | 9.7 | 42.6 |
| Selectivity, % | | | | | | | |
| cis-stilbene | 6.6 | 7.7 | 7.6 | 6.3 | 4.6 | 3.5 | 5.5 |
| trans-stilbene | 56.5 | 65.9 | 62.2 | 51.8 | 37.5 | 29 | 44.6 |
| Bibenzyl | 3.2 | 6.7 | 11.4 | 30.2 | 47.5 | 55 | 22.6 |
| Benzene | 21.3 | 10.4 | 9.9 | 5.3 | 4.3 | 5.7 | 15.1 |
| $CO_2$ | 3.2 | 1.5 | 1.2 | 0.7 | 0.7 | 1.4 | 4.4 |

EXAMPLE 7

A metal- and oxygen-containing composition prepared as in Example 5 and having the same Sb/Pb/Bi atomic ratio (1:1.5:0.25) was employed as a catalyst for dehydrocoupling toluene to stilbene. Following the same procedure as in the previous examples, oxygen was fed as air at a rate of 80 ml/min. over 18 ml (25g) of catalyst along with the steam and hydrocarbon (molar ratio 2:1) in the several runs carried out at 580° C. at a contact time of 0.85 second. Results obtained under these conditions over the several different reaction periods employed are presented in Table 7 below.

Table 7

| Run No. | 1 | 2 | 3 |
| --- | --- | --- | --- |
| Reaction Time, min. | 3 | 40 | 70 |
| Conversion, % | 35.5 | 28 | 30 |
| Selectivity, % | | | |
| cis-stilbene | 3.4 | 2.69 | 2.9 |
| trans-stilbene | 28.2 | 22 | 23.6 |
| Bibenzyl | 30.2 | 30.6 | 31.1 |
| Benzene | 17.4 | 19.4 | 18.1 |
| $CO_2$ | 15.7 | 20.4 | 18.6 |

What is claimed is:

1. As an oxidant or catalyst for dehydrocoupling of toluene and toluene derivatives to produce stilbene and stilbene derivatives, the antimony, lead, bismuth and oxygen-containing composition having the formula $$Sb_a Pb_b Bi_c O_d$$

wherein a is 1, b is 0.2 to 10, C is a positive number up to 5 and d is a number taken to satisfy the average valences of the Sb, Pb and Bi in the oxidation states in which they exist in said composition.

2. As an oxidant or catalyst for the dehydrocoupling of toluene to stilbene, the antimony, lead, bismuth and oxygen-containing composition having the formula $$Sb_a Pb_b Bi_c O_d$$

wherein a is 1, b is 0.5 to 5, c is a positive number up to 1 and d is a number taken to satisfy the average valences of the Sb, Pb and Bi in the oxidation states in which they exist in said composition.

* * * * *